(12) United States Patent
Cayota Guzicovsky et al.

(10) Patent No.: US 7,371,569 B2
(45) Date of Patent: May 13, 2008

(54) METHODS FOR PREPARING HUMAN THROMBOPOIETIN POLYPEPTIDES BY MAMMALIAN CELL CULTURES

(76) Inventors: Alfonso Cayota Guzicovsky, 77 M 201-S 14, Solymar, Canelones (UY); Carlos Alberto Robello Porto, 26 de Marzo 3283 Piso 004, Montevideo (UY); Otto Franz Pritsch Albisu, Guana 1975, Montevideo (UY)

(*) Notice: Subject to any disclaimer, the term of this patent is extended or adjusted under 35 U.S.C. 154(b) by 373 days.

(21) Appl. No.: 10/362,882

(22) PCT Filed: Aug. 23, 2001

(86) PCT No.: PCT/IB01/01518

§ 371 (c)(1),
(2), (4) Date: Oct. 10, 2003

(87) PCT Pub. No.: WO02/18569

PCT Pub. Date: Mar. 7, 2002

(65) Prior Publication Data

US 2004/0072326 A1    Apr. 15, 2004

(30) Foreign Application Priority Data

Aug. 30, 2000   (UY) ................................ 26317

(51) Int. Cl.
*C12N 15/00* (2006.01)

(52) U.S. Cl. .................. 435/320.1; 435/69.1; 435/325; 435/354

(58) Field of Classification Search ..................... None
See application file for complete search history.

(56) References Cited

U.S. PATENT DOCUMENTS 5,019,499 A * 5/1991 Murakami et al. ......... 435/69.1
6,015,662 A * 1/2000 Hackett et al. ................ 435/5

OTHER PUBLICATIONS

Picard et al., EMBO 4: 2831-2838, 1985.*
Polack et al., EMBO 12:3913-3920, 1993.*
Kearney et al., J. Immunol. 123:1548-1550 1979.*
Dumas, Gerard et al., "A murine model of human cold agglutinin disease", British Journal of Haematology, 1997, pp. 589-596.

* cited by examiner

*Primary Examiner*—Robert S. Landsman
*Assistant Examiner*—Gyan Chandra
(74) *Attorney, Agent, or Firm*—McDermott Will & Emery LLP

(57) ABSTRACT

Procedures to produce a biologically active human TPO by mammalian cells in in vitro cultures are disclosed. Murine myeloma cells were genetically modified by introducing the gene of human thrombopoietin through a DNA construction which includes an immunoglobulin promoter associated to an immunoglobulin enhancer. The hTPO obtained is useful with methods of stimulating proliferation or development of hematopoietic cells of the megakaryocytic leneage in vitro and in vivo.

3 Claims, 3 Drawing Sheets

FIGURE 1. Schematic description of the expression vector pK-eTPO.
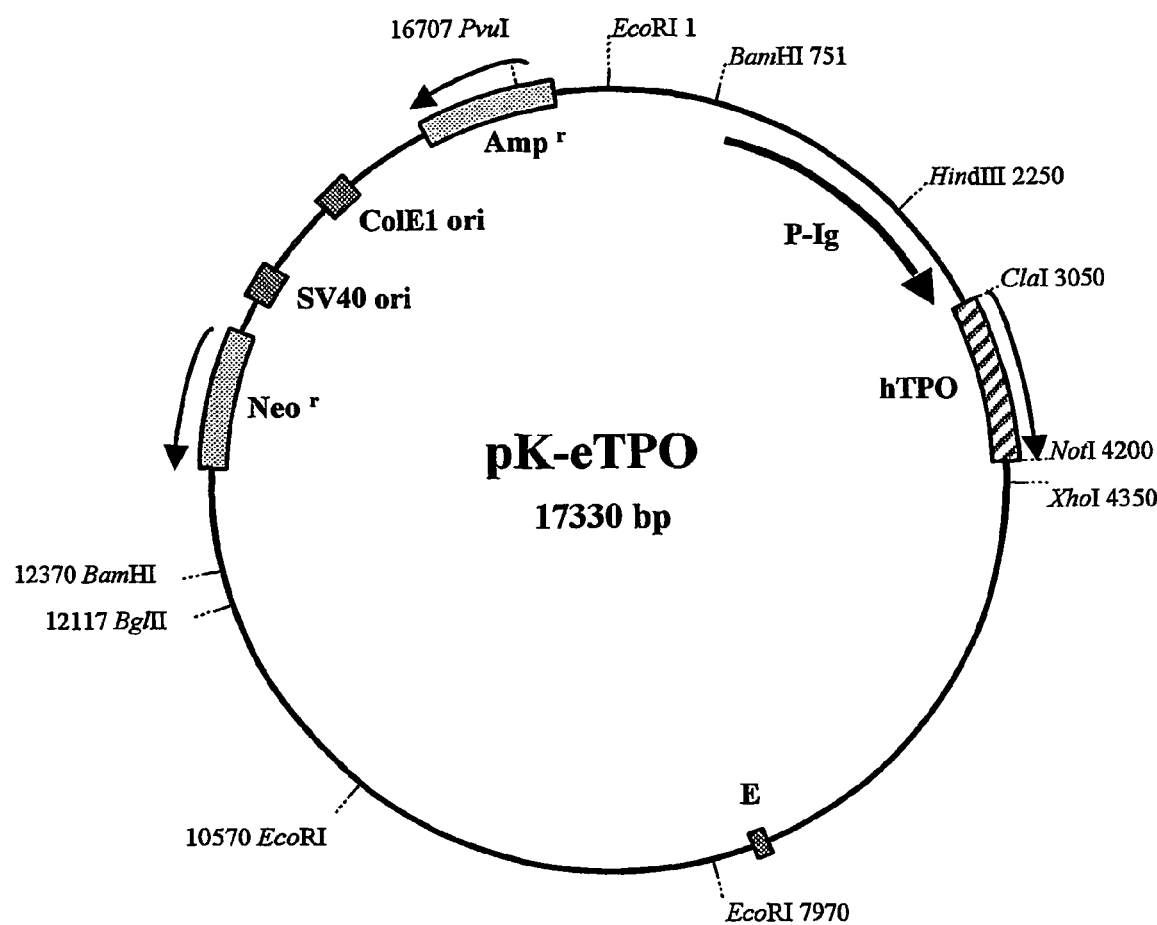
E: Immunoglobulin enhancer; P-Ig: Immunoglobulin promoter FIGURE 2. Anti-hTPO western blot assay of subclone 16 from clone 2A4 (2A4/16). Evaluation of stability and production levels of rhTPO.
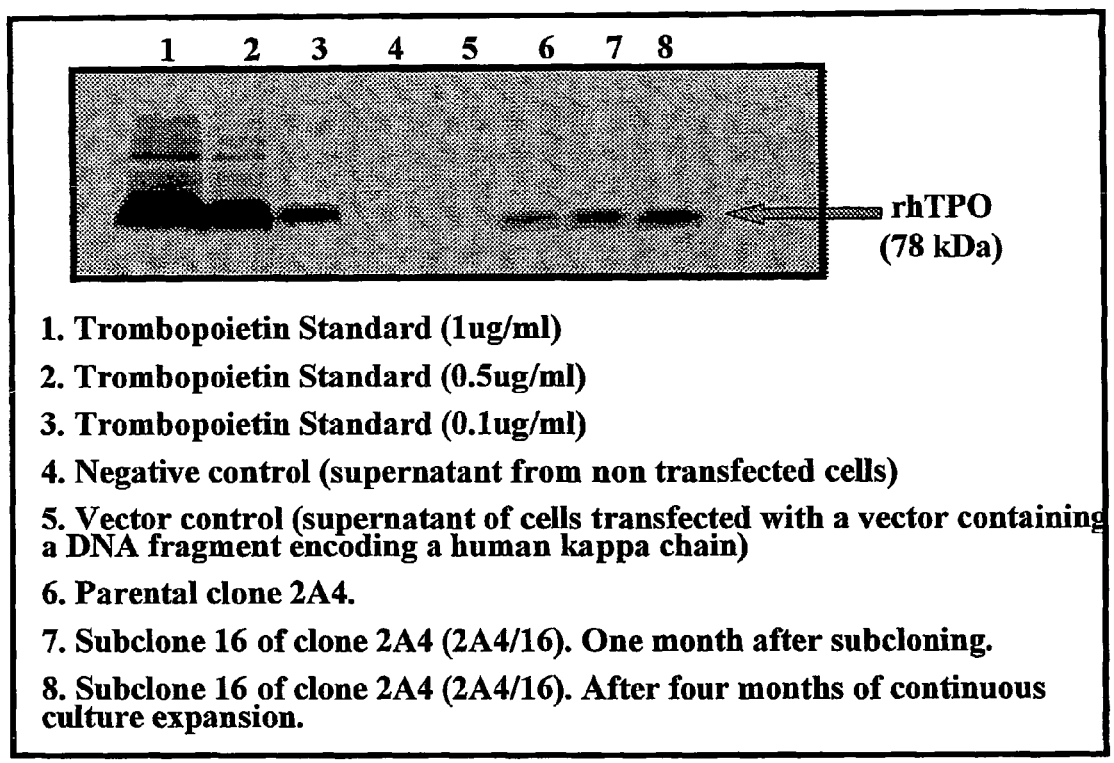

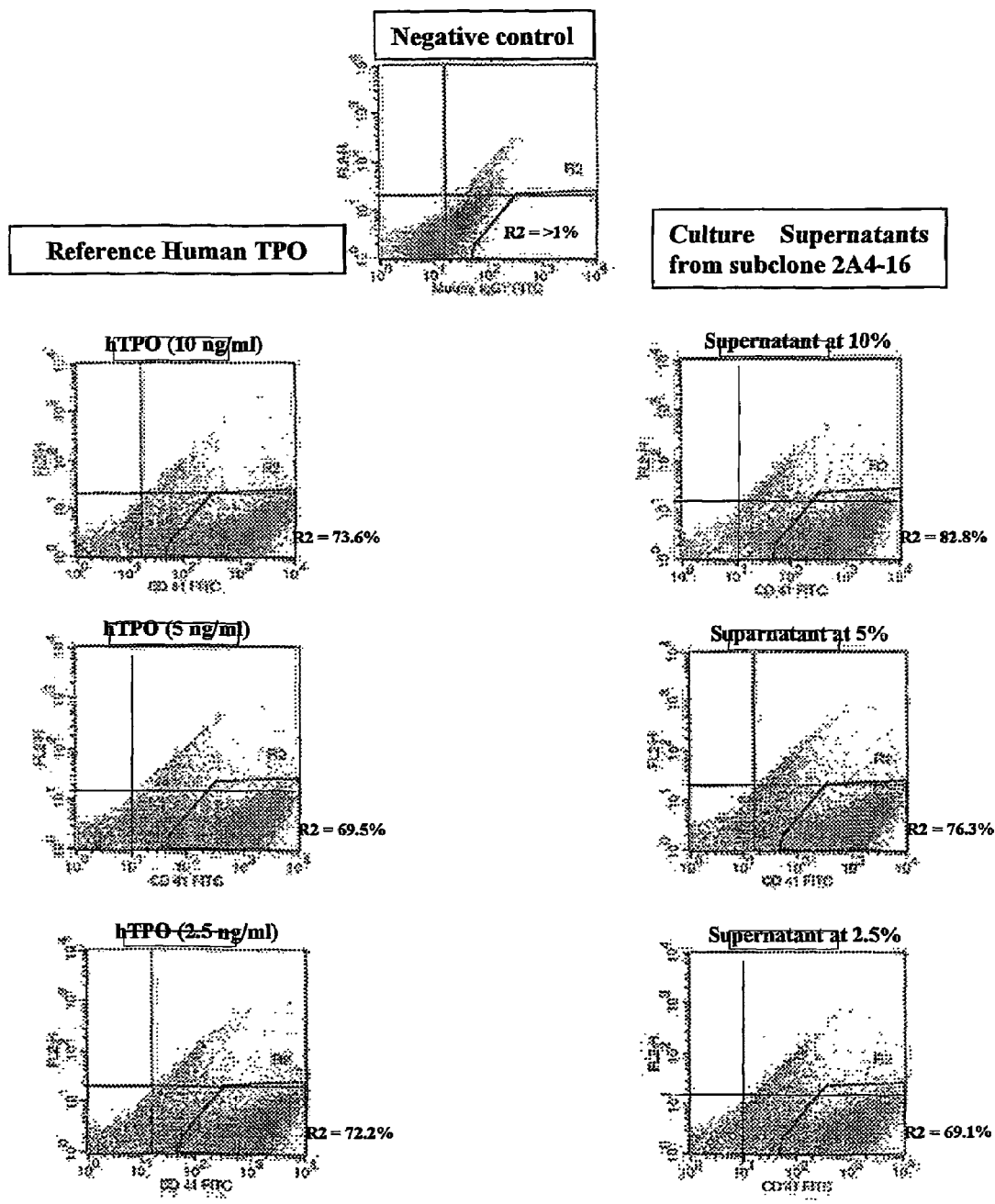
FIGURE 3. Flow cytometry analysis of *in vitro* CD41 expression induced by supernatants from hTPO producer clones on cells from human bone marrow. Results are compared to those obtained with a human TPO standard

SEQUENCE LISTING

<160> NUMBER OF SEQ ID NOS: 8

<210> SEQ ID NO 1
<211> LENGTH: 1090
<212> TYPE: DNA
<213> ORGANISM: Homo sapiens
<220> FEATURE:
<221> NAME/KEY: primer_bind
<222> LOCATION: (1)..(39)
<220> FEATURE:
<221> NAME/KEY: CDS
<222> LOCATION: (18)..(1079)
<220> FEATURE:
<221> NAME/KEY: sig_peptide
<222> LOCATION: (18)..(80)
<220> FEATURE:
<221> NAME/KEY: primer_bind
<222> LOCATION: (1054)..(1090)

<400> SEQUENCE: 1

```
catatcgatt tctcaca atg gag ctg act gaa ttg ctc ctc gtg gtc atg          50
                   Met Glu Leu Thr Glu Leu Leu Leu Val Val Met
                    1               5                  10 ctt ctc cta act gca agg cta acg ctg tcc agc ccg gct cct cct gct         98
Leu Leu Leu Thr Ala Arg Leu Thr Leu Ser Ser Pro Ala Pro Pro Ala
                15                  20                  25 tgt gac ctc cga gtc ctc agt aaa ctg ctt cgt gac tcc cat gtc ctt        146
Cys Asp Leu Arg Val Leu Ser Lys Leu Leu Arg Asp Ser His Val Leu
            30                  35                  40 cac agc aga ctg agc cag tgc cca gag gtt cac cct ttg cct aca cct        194
His Ser Arg Leu Ser Gln Cys Pro Glu Val His Pro Leu Pro Thr Pro
        45                  50                  55 gtc ctg ctg cct gct gtg gac ttt agc ttg gga gaa tgg aaa acc cag        242
Val Leu Leu Pro Ala Val Asp Phe Ser Leu Gly Glu Trp Lys Thr Gln
60                  65                  70                  75 atg gag gag acc aag gca cag gac att ctg gga gca gtg acc ctt ctg        290
Met Glu Glu Thr Lys Ala Gln Asp Ile Leu Gly Ala Val Thr Leu Leu
                80                  85                  90 ctg gag gga gtg atg gca gca cgg gga caa ctg gga ccc act tgc ctc        338
Leu Glu Gly Val Met Ala Ala Arg Gly Gln Leu Gly Pro Thr Cys Leu
            95                 100                 105 tca tcc ctc ctg ggg cag ctt tct gga cag gtc cgt ctc ctc ctt ggg        386
Ser Ser Leu Leu Gly Gln Leu Ser Gly Gln Val Arg Leu Leu Leu Gly
        110                 115                 120 gcc ctg cag agc ctc ctt gga acc cag ctt cct cca cag ggc agg acc        434
Ala Leu Gln Ser Leu Leu Gly Thr Gln Leu Pro Pro Gln Gly Arg Thr
    125                 130                 135 aca gct cac aag gat ccc aat gcc atc ttc ctg agc ttc caa cac ctg        482
Thr Ala His Lys Asp Pro Asn Ala Ile Phe Leu Ser Phe Gln His Leu
140                 145                 150                 155 ctc cga gga aag gtg cgt ttc ctg atg ctt gta gga ggg tcc acc ctc        530
Leu Arg Gly Lys Val Arg Phe Leu Met Leu Val Gly Gly Ser Thr Leu
                160                 165                 170 tgc gtc agg cgg gcc cca ccc acc aca gct gtc ccc agc aga acc tct        578
Cys Val Arg Arg Ala Pro Pro Thr Thr Ala Val Pro Ser Arg Thr Ser
            175                 180                 185 cta gtc ctc aca ctg aac gag ctc cca aac agg act tct gga ttg ttg        626
Leu Val Leu Thr Leu Asn Glu Leu Pro Asn Arg Thr Ser Gly Leu Leu
        190                 195                 200 gag aca aac ttc act gcc tca gcc aga act act ggc tct ggg ctt ctg        674
Glu Thr Asn Phe Thr Ala Ser Ala Arg Thr Thr Gly Ser Gly Leu Leu
    205                 210                 215
```

-continued

| | | |
|---|---|---|
| aag tgg cag cag gga ttc aga gcc aag att cct ggt ctg ctg aac caa<br>Lys Trp Gln Gln Gly Phe Arg Ala Lys Ile Pro Gly Leu Leu Asn Gln<br>220                       225                    230                 235 | 722 |
| acc tcc agg tcc ctg gac caa atc ccc gga tac ctg aac agg ata cac<br>Thr Ser Arg Ser Leu Asp Gln Ile Pro Gly Tyr Leu Asn Arg Ile His<br>                  240                    245                    250 | 770 |
| gaa ctc ttg aat gga act cgt gga ctc ttt cct gga ccc tca cgc agg<br>Glu Leu Leu Asn Gly Thr Arg Gly Leu Phe Pro Gly Pro Ser Arg Arg<br>                      255                    260                  265 | 818 |
| acc cta gga gcc ccg gac att tcc tca gga aca tca gac aca ggc tcc<br>Thr Leu Gly Ala Pro Asp Ile Ser Ser Gly Thr Ser Asp Thr Gly Ser<br>270                       275                    280 | 866 |
| ctg cca ccc aac ctc cag cct gga tat tct cct tcc cca acc cat cct<br>Leu Pro Pro Asn Leu Gln Pro Gly Tyr Ser Pro Ser Pro Thr His Pro<br>         285                    290                  295 | 914 |
| cct act gga cag tat acg ctc ttc cct ctt cca ccc acc ttg ccc acc<br>Pro Thr Gly Gln Tyr Thr Leu Phe Pro Leu Pro Pro Thr Leu Pro Thr<br>300                       305                    310                 315 | 962 |
| cct gtg gtc cag ctc cac ccc ctg ctt cct gac cct tct gct cca acg<br>Pro Val Val Gln Leu His Pro Leu Leu Pro Asp Pro Ser Ala Pro Thr<br>                  320                    325                  330 | 1010 |
| ccc acc cct acc agc cct ctt cta aac aca tcc tac acc cac tcc cag<br>Pro Thr Pro Thr Ser Pro Leu Leu Asn Thr Ser Tyr Thr His Ser Gln<br>                     335                    340                  345 | 1058 |
| aat ctg tct cag gaa ggg taa gcggccgctc t<br>Asn Leu Ser Gln Glu Gly<br>         350 | 1090 |

<210> SEQ ID NO 2
<211> LENGTH: 353
<212> TYPE: PRT
<213> ORGANISM: Homo sapiens

<400> SEQUENCE: 2

Met Glu Leu Thr Glu Leu Leu Val Val Met Leu Leu Leu Thr Ala
1                   5                       10                      15

Arg Leu Thr Leu Ser Ser Pro Ala Pro Ala Cys Asp Leu Arg Val
                    20                    25                    30

Leu Ser Lys Leu Leu Arg Asp Ser His Val Leu His Ser Arg Leu Ser
                35                    40                    45

Gln Cys Pro Glu Val His Pro Leu Pro Thr Pro Val Leu Leu Pro Ala
        50                    55                    60

Val Asp Phe Ser Leu Gly Glu Trp Lys Thr Gln Met Glu Glu Thr Lys
65                  70                    75                    80

Ala Gln Asp Ile Leu Gly Ala Val Thr Leu Leu Leu Glu Gly Val Met
                85                    90                    95

Ala Ala Arg Gly Gln Leu Gly Pro Thr Cys Leu Ser Ser Leu Leu Gly
                  100                   105                 110

Gln Leu Ser Gly Gln Val Arg Leu Leu Leu Gly Ala Leu Gln Ser Leu
              115                   120                   125

Leu Gly Thr Gln Leu Pro Pro Gln Gly Arg Thr Thr Ala His Lys Asp
          130                   135                  140

Pro Asn Ala Ile Phe Leu Ser Phe Gln His Leu Leu Arg Gly Lys Val
145                 150                 155                  160

Arg Phe Leu Met Leu Val Gly Gly Ser Thr Leu Cys Val Arg Arg Ala
                  165                   170                 175

Pro Pro Thr Thr Ala Val Pro Ser Arg Thr Ser Leu Val Leu Thr Leu

-continued

```
                    180                 185                 190

Asn Glu Leu Pro Asn Arg Thr Ser Gly Leu Leu Glu Thr Asn Phe Thr
        195                 200                 205

Ala Ser Ala Arg Thr Thr Gly Ser Gly Leu Leu Lys Trp Gln Gln Gly
        210                 215                 220

Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
                245                 250                 255

Thr Arg Gly Leu Phe Pro Gly Pro Ser Arg Arg Thr Leu Gly Ala Pro
            260                 265                 270

Asp Ile Ser Ser Gly Thr Ser Asp Thr Gly Ser Leu Pro Pro Asn Leu
        275                 280                 285

Gln Pro Gly Tyr Ser Pro Ser Pro Thr His Pro Pro Thr Gly Gln Tyr
        290                 295                 300

Thr Leu Phe Pro Leu Pro Pro Thr Leu Pro Thr Pro Val Val Gln Leu
305                 310                 315                 320

His Pro Leu Leu Pro Asp Pro Ser Ala Pro Thr Pro Thr Pro Thr Ser
                325                 330                 335

Pro Leu Leu Asn Thr Ser Tyr Thr His Ser Gln Asn Leu Ser Gln Glu
            340                 345                 350

Gly

<210> SEQ ID NO 3
<211> LENGTH: 22
<212> TYPE: DNA
<213> ORGANISM: Artificial Sequence
<220> FEATURE:
<223> OTHER INFORMATION: TPOext-fow (External forward primer)

<400> SEQUENCE: 3
caggaaggat tcagggaga gg                                              22

<210> SEQ ID NO 4
<211> LENGTH: 22
<212> TYPE: DNA
<213> ORGANISM: Artificial Sequence
<220> FEATURE:
<223> OTHER INFORMATION: TPOext-rev (External reverse primer)

<400> SEQUENCE: 4
ggaagggagc tgtacatgag ac                                             22

<210> SEQ ID NO 5
<211> LENGTH: 22
<212> TYPE: DNA
<213> ORGANISM: Artificial Sequence
<220> FEATURE:
<223> OTHER INFORMATION: TPOfow (Internal forward primer)

<400> SEQUENCE: 5
agccacgcca gccagacacc cc                                             22

<210> SEQ ID NO 6
<211> LENGTH: 22
<212> TYPE: DNA
<213> ORGANISM: Artificial Sequence
<220> FEATURE:
<223> OTHER INFORMATION: TPOrev (Internal reverse primer)

<400> SEQUENCE: 6
```

```
gcagtgtctg agaaccttac cc                                          22

<210> SEQ ID NO 7
<211> LENGTH: 39
<212> TYPE: DNA
<213> ORGANISM: Artificial Sequence
<220> FEATURE:
<223> OTHER INFORMATION: Cla-eTPOfow primer

<400> SEQUENCE: 7
catatcgatt tctcacaatg gagctgactg aattgctcc                        39

<210> SEQ ID NO 8
<211> LENGTH: 37
<212> TYPE: DNA
<213> ORGANISM: Artificial Sequence
<220> FEATURE:
<223> OTHER INFORMATION: Not-eTPOrev primer

<400> SEQUENCE: 8
agagcggccg cttacccttc ctgagacaga ttctggg                          37
```

METHODS FOR PREPARING HUMAN THROMBOPOIETIN POLYPEPTIDES BY MAMMALIAN CELL CULTURES

BACKGROUND OF THE INVENTION

In every normal adult, blood cells are produced at the bone marrow from stem cells through a process called "hematopoiesis". After several steps of proliferation and differentiation, those progenitor pluripotent cells are capable of autoduplicating without differentiating themselves (endoduplication/autoreplication) or capable of generating a series of progenitor cells grouped in 4 principal ways of differentiation: a) erythroid (red blood cells or erythrocytes); b) myeloid (polimorphonuclear leucocytes and monocytes); c) lymphoid (lymphocytes) and d) megakaryiotic (generator of megakaryocytes/platelets). The quantity and cellular type produced by the bone marrow is a process finely regulated by a complex network of cytokines or growth factors that act via membrane-bound receptors on the target cells. These cytokines include a heterogeneous group of growth factors including interleukins (among others TNF-α, IL-3, IL-6, IL-8 e IL-11) and glycoproteic hormones called "Colony Stimulating Factors" (Granulocyte Colony stimulating factors and Granulocyte/Macrophage Colony stimulating factors [G-CSF y GM-CSF respectively]); Erythropoietin as stimulation factor of erythrocyte progenitors and Thrombopoietin as stimulator of platelet progenitors.

An increased knowledge of hematopoiesis and its regulation has lead to the use of diverse hematopoietic cytokines in medical treatment. In this way, medical treatments have been included based on:

Erythropoietin (EPO) for the treatment of secondary anemia in chronic kidney failure.

Colony stimulating factors (G-CSF y GM-CSF) to accelerate the recovery of the immune system in cancer patients undergoing chemotherapy or those receiving a bone marrow transplant.

IL-2 and Interferon-α Both have been widely used in conjunction with chemotherapeutic agents. Interferons are being used, with certain success, in the treatment of chronic hepatitis, as well as IL-2 in AIDS associated to antiretroviral agents.

The circulating blood platelets are produced in the bone marrow and play a crucial role in blood coagulation. Platelets adhere to sites of tissue damage and recruit others to aggregate with it to form the "primary hemostatic plug". In addition, it serves as the surface upon which the coagulation factors are activated to produce a fibrin clot. In the absence of platelets, both of these functions are deficient and bleeding ensues (1). The generation of platelets implies proliferation and differentiation of bone marrow stem cells, into megakaryocytic cells which will generate the mature platelets (thrombocytes) that normally circulate in peripheral blood.

The physiological process by which platelets are generated requires the presence of factors called "Thrombocytopoietic" as growth and development factors from the megakaryocytic-lineage. In clinical medicine, the decrease of the number of platelets (thrombocytopenia) is a great complication related to two relevant situations: a) diseases that affect the normal generation of platelets (primary thrombocytopenia) and B) as a result of complications derived form therapeutic treatment in cancer patients or patients that have received a bone marrow transplant (secondary thrombocytopenia). The increased risk of hemorrhages in these patients actually requires the administration of platelet concentrates from normal donors with the associated biological risk (allergies, infections, immune hypersensitivity). From the early description in 1958, of a thrombopoietin activity in thrombocytopenic animals by Kelemen and cols. (2), we had to wait until 1994 in order to identify that factor, that was purified and cloned by several groups, as a glycoprotein capable of binding the cellular receptor Mpl (oncogene responsible of the murine myeloproliferative leukemia virus) (3) that was identified as Thrombopoietin (alternatively called: c-Mpl ligand; Megapoietin or Megakaryocyte Growth and Development Factor (MGDF)) able to specifically stimulate the megakaryocytopoiesis or thrombocytopoiesis (4-8). Other factors with thrombopoietic activity have been described (9), including IL-6 and IL-11 although they are not specific and have pleiotropic actions. The administration of high doses of IL-11 and IL-6 isolatedly, have resulted in low increments of circulating platelets (10) The gene of Human Thrombopoietin (hTPO) has been localized as a single copy, to chromosome 3 (3q26-27). It codifies for a protein of 353 amino acids (open reading frame of 10590 base pairs), including a signal peptide of 21 amino acids (aa) (63 base pairs). The mature protein has 332 aa (996 bp) and an estimated molecular weight of 38 kDa (not glycosilated). It has 6 N-glycosilation sites in order to generate a complete glycosilated protein of 70-80 kDa and a cleavage site, between arginines 153 and 154, where the protein is divided into two domains: a) a highly glycosilated c-terminal domain without homology with known proteins, and b) an EPO-like or N-terminal domain of 153 aa with 23% of identity with EPO. Allowing for conservative aa substitutions, sequence conservation approaches 50%. It is important to highlight that the non-glycosilated form has complete activity in vitro but not in vivo due to a decreased stability and a quick depuration in the circulation. Besides the native molecule (70-80 kDa), several forms of circulating TPO have been described, as a result of its partial proteolysis consisting of forms of 30,25 and 18 kDa, all truncated at the C-terminal domain (9, 11 and 12).

At present, the only factor with thrombocytopoietic activity available and approved by the FDA (Food and Drug Administration) is the human recombinant IL-11.

GENERAL DESCRIPTION OF THE INVENTION

From a general point of view this invention concerns:

Within one aspect, the present invention provides an expression vector replicable in mammalian host cells. The vectors comprise the following operably linked elements: 1) a transcription promoter; 2) the first DNA segment encoding a secretory leader or signal peptide of native hTPO; 3) a second DNA segment encoding the complete hTPO polypeptide; 4) a transcriptional enhancer; 5) polyadenylation signal and 6) a transcription terminator.

Within a second aspect of the invention, there is provided a cultured eukaryotic cell line containing the DNA construct as disclosed above. The prefered cell line is a mammalian cell.

Within a third aspect, there is provided a description of hTPO production procedure that has a murine cell line of plasmocytic origin, transfected with the espression vector previously described. Thus, this cell line acquires the capacity to synthesize and secrete a biologically active human recombinant hTPO (rhTPO), identical to its natural counterpart.

DETAILED DESCRIPTION OF THE INVENTION

Prior to describing the present invention and in order to facilitate its comprehension, it may be helpful to make a description summarizing and explaining some of the terms and procedures used in the present invention:

Thrombopoietin (TPO) It is a glycoprotein mainly produced by hepatic and kidney cells in normal individuals. It is capable to specifically bind to Mpl receptor from the same species stimulating platelet production. Mpl receptor is mainly present on pluripotent stem cells, megakaryocytes and platelets. The prefix "h" makes reference to human TPO (hTPO). The term hTPO encompasses full-length thrombopoietin molecules that exhibit the qualitative biological activities of the intact molecule (receptor binding and in vivo stimulation of platelet production).

Recombinant Protein When a cell from a certain origin is genetically modified, through recombinant DNA techniques, in order to produce a protein that is not normally produced by it, acquires the name of recombinant protein. Generally the prefix "r" indicated that it is a recombinant biomolecule.

cDNA (Complementary Deoxyribonucleic Acid). Represents a complementary copy of ribonucleic Acid (RNA) obtained by a process called reverse transcription, by which a DNA polimerase uses RNA as template (reverse transcriptase). The cDNA can be single-stranded or double-stranded.

Expression Vector Is a DNA molecule, linear or circular, that comprises a segment encoding a polypepetide of interest operably linked to additional segments that provide for its transcription. Such additional segments include promoter and temrinator sequences. An expression vector may also include one or more origins of replication, one or more selectable markers, an enhancer, a polyadenylation signal, etc. Expression vectors are generally derived from plasmid or viral DNA, or may contain elements of both. The term "operably linked" indicates that the segments are arranged so that they function in concert for their intended purposes, e.g. transcription initiates in the promoter and proceeds through the coding segment to the terminator. Replication of expression vectors in a host organism can be autonomous or through integration into the host genome.

Leader or signal sequence A DNA sequence encoding a secretory peptide. Signal sequences are also called leader or prepro sequences. A secretory peptide is an amino acid sequence that acts to direct the secretion of a mature polypeptide or protein from a cell. Secretory peptides are characterized by a core of hydrophobic amino acids and are typically (but not exclusively) found at the amino termini of newly synthesized proteins. Very often the secretory peptide is cleaved from the mature protein during secretion in one or more cleavage events. Such secretory peptides contain processing sites that allow cleavage of the secretory peptides from the mature proteins as they pass through the secretory pathway.

Promoter DNA sequence recognized by RNA polimerase in order to initiate the gene transcription and generate the corresponding messenger RNA.

Transfection It is the process by which an eukaryotic cell is genetically modified through the introduction of DNA constructions that are capable of producing a protein that is not normally produced by that cell. They are described as "transfected cells".

The present invention provides the material and methods used in order to obtain a human recombinant TPO with proved biological activity and whose general experimental design had the following steps:

1. Total RNA was isolated from normal human liver obtained from a volunteer donor who had hepatobilliar surgery.
2. Total cDNA was obtained from RNA by a process of reverse transcription and the complete sequence of hTPO was amplified from cDNA by using specific primers (Table II).
3. We proceed to the construction of an expression vector containing the specific cDNA of hTPO, in a form capable of being introduced in an eukaryotic cell in order to induce the expression and production of Human Thrombopoietin.
4. That vector is introduced, by conventional electroporation techniques, in a mammalian cell line that can be cultivated in vitro.
5. Neomycin antibiotic is added to the artificial medium in which cells are grown. The cells that have successfully incorporated the expression vector are selected because they bear the gene enconding resistance to the antibiotic neomycin.
6. By limited dilution methods, individual cells that host the expression vector are selected. Cells producing a significant amount of recombinant human Thrombopoietin are called "Clones".
7. Its biological activity is tested in in vitro and in vivo assays using culture supernatants, by their ability to alternatively induce: a) the differentiation of hematopoietic precursors towards megakaryocytes in in vitro cultures; b) proliferation of TPO-dependant cell lines; c) increase in circulating blood platelets in thrombocytopenic animals (in vivo stimulation of platelet production).

The nucleotide sequence identified as NM000460 and the aminoacidic sequence identified as SEQ N°1 that corresponds to the mature hTPO is represented in Table I (5). The sequences NM 000460 and SEQ N°1 represent a single allele of hTPO from which different allele variants may exist. Those variants can be obtained from cloned cells, human tissues or DNA preparations. That sequence was used to obtain primers necessary to amplify the specific TPO material and its posterior cloning and purification. In the present invention we proceed to clone and obtain the cDNA that corresponds to the complete hTPO including its signal peptide from normal hepatic tissue. No partial or modified fragments of the same sequence were used in the present invention.

The expression vector constructed in this invention (replicable in mammalian cells), as previously described, sequentially contains: a) a transcription promoter, derived from a variable gene from a kappa chain of human immunoglobulins obtained from a genomic library of human B lymphocytes; b) a first segment of DNA encoding the specific signal peptide of hTPO; c) a second segment of DNA encoding the full-length mature hTPO polypeptide; d) a transcriptional enhancer, derived from an intronic region from a human kappa gene (obtained from a genomic library of human B lymphocytes); e) a polyadenylation signal; f) a transcription terminator; g) the complete sequence of the resistance gene to ampicillin, as a selection marker in bacterial systems; h) the complete sequence of the resistance gene to neomycin, as a selection marker in eukaryotic cell systems; I) a bacterial replication origin that allows its expansion in bacteria. The direct product of transcription and transduction of the DNA segment that codes the mature hTPO polypeptide may depend on a post-transductional processing adding different chemical groups that include, among others, the union of carbohydrates through chemical bonds called "N-linked glycosilation or O-linked glycosilation". The exact nature of this post-transductional modifications will be determined mostly but not exclusively, by the type of host cell used to produce recombinant hTPO.

Suitable host cells for use within the present invention include any type of eukaryotic cell that can be engineered to express heterologous DNA, can be grown in culture, and has an efficient secretory pathway. The preferred cells that follow these requirements are those derived from murine myeloma which are kown in the art and available from public depositories such as the American Type Culture Collection, Rockville, Md. (ATCC). In order to give a reference, the line X-63 (P63X63Ag.563 (ATCC N° CRL-1580) and SP2 (ATCC N° CRL-1581 and CRL-8287). In order to direct a hTPO plypeptide into the secretory pathway of the host cell, a DNA sequence encoding a secretory leader is used in combination with a DNA sequence encoding a hTPO polypeptide. In the present invention the signal peptide used was the corresponding to native hTPO (aminoacidic sequence appears in bolded font over SEQ 1 in Table I). Generally strong promoters of transcription are required, such as immunglobulins, viral promoters derived from SV40, adenovirus or citomegalovirus that are included here in order to have a reference.

Drug selection is a widely used method that allows selecting those mammalian culture cells that have successfully incorporated the expression vector. Such cells are commonly referred to as "transfectants". Cells that have been cultured in the presence of the selective agent and are able to pass the gene of interest to their progeny are referred to as "stable transfectants". A preferred selectable marker is a gene encoding resistance to the antibiotic neomycin. Selection is carried out in the presence of neomycin-type drug, such as G-418 or the like. Selection systems may also be used to increase the expression level of the gene of interest, a process referred to as "amplification". Amplification is carried out by culturing transfectants in the presence of a low level of the selective agent and then increasing the amount of selective agent to select for cells that produce high levels of the products of the introduced genes. Other drug resistance genes that can be used may be the hygromycine, multi-drug resistance gene, dihydrofolate reductase and puromycin acetyltransferase.

There are many methods to incorporate exogenous DNA into mammalian cells, among which we highlight: a) calcium phosphate-mediated transfection; b) electroporation (14); c) DEAE-dextrane mediated transfection (Ausubel et al., eds. Current Protocols in Molecular Biology, John Wiley and Sons, Inc., NY, 1987) and d) cationic lipid-mediated transfection. The preferred method used in the present invention is electroporation. The transfected cells are cultured in conventional media, which contain essential nutrients for cellular growth, as well as the necessary antibiotics in order to select the cells that have incorporated exogenous DNA.

The hTPO polypeptide prepared according to the present invention can be used therapeutically wherever it is desirable to increase platelet production, such as in the treatment of thrombocytopenia induced by different diseases including aplastic anemia, myelodisplastic syndromes, chemotherapy or congenital thrombocytopenias.

The thrombocytopenia is characterized by a decrease in the number of circulating blood platelets and is manifested as increased skin and mucosal bleedings. Lowered platelet counts can result from, for example, defects in platelet production, abnormal platelet distribution, dilutional losses due to massive transfusions, or abnormal destruction of platelets. In addition, certain malignancies can impair platelet production and platelet distribution. Radiation therapy used to kill malignant cells also kills platelet progenitor cells. Thrombocytopenia may also arise from various platelet autoimmune disorders induced by drugs, neonatal alloimmunity or platelet transfusion alloimmunity. hTPO polypeptides can reduce or eliminate the need for transfusion, thereby reducing the incidence of platelet alloimmunity. Abnormal destruction of platelets can result from: 1) increased platelet consumption in vascular grafts or traumatized tissue; or 2) immune mechanisms associated with, for example, drug-induced thromocytopenia, idiopathic thrombocytopenic purpura (ITP), autoimmune diseases, hematologic disorders such as leukemia and lymphoma, or metastatic cancers involving bone marrow. Other indications for hTPO include aplastic anemia and rug-induced marrow suppression resulting from, for example, chemotherapy or treatment of HIV infection with AZT.

rhTPO can be also associated with other cytokines such as SCF, IL-3, IL-6, IL-11 or GM-CSF. The therapeutic doses of rhTPO are in the range of 0.1 a 100 µg/kg per day (preferably 0.5-50 µg/kg a day). The exact doses must be determined by clinical evaluation in each particular case. The rhTPO is administered for a 28 day period following chemotherapy or bone marrow transplant, or until the number of platelets is more than 20.000/µl, preferably 50.000/µl.

rhTPO polypeptides are also valuable tools for the in vitro study of the differentiation and development of hematopoietic cells, such as for elucidating the mechanisms of cell differentiation and for determining the lineages of mature cells, and may also find utility as a proliferative agent in cell culture.

rhTPO polypeptides can also be used ex vivo, such as in autologous marrow culture. Briefly, bone marrow is removed from a patient prior to chemotherapy and treated with rhTPO polypeptides, optionally in combination with one or more other cytokines. The treated marrow is then returned to the patient after chemotherapy to speed the recovery fo the marrow. In addition, rhTPO polypeptides can also be used for the ex vivo expansion of marrow or peripheral blood progenitor (PBPC) cells. Prior to chemotherapy treatment, marrow can be stimulated with stem cell factor (SCF) or G-CSF to release early progenitor cells into peripheral circulation. These progenitors can be collected and concentrated from peripheral blood and then treated in culture with one or more rhTPO polypeptides, optionally in combination with one or more other cytokines, cinluding but not limited to SCF, G-CSF, IL-3, GM-CSF, IL-6 or IL-11, to differentiate and proliferate into high-density megakaryocyte cultures, which can then be retured to the patient following high-dose chemotherapy.

Another potential use of rhTPO, is its use in several diagnostics that are performed in order to determine the presence of anti-TPO antibodies, which have been demonstrated in autoimmune thrombocytopenias.

The present invention is futher illustrated by the following non-limiting examples.

EXAMPLES

Example 1 mRNA obtained from hepatic tissue of a normal adult in order to obtain specific cDNA of hTPO. A fragment of hepatic tissue from a normal adult (50 mgrs) was processed in order to isolate total RNA. This process was performed applying classical methods of extraction with guanidine thiocyanate phenol-chloroform. The purity and concentration of total RNA was determined by 260/280 absorbance ratio.

Example 2 cDNA synthesis (reverse transcription) of hTPO specific mRNA. Synthesis of the first stand of cDNA by reverse transcription, was performed from 5 ug of total RNA, using synthetic Oligo(dT)$_{12-18}$ and Reverse Transcriptase (SUPERSCRIPT™ II, Gibco-BRL-Life Technologies). The assay was performed in a total volume of 20 µl containing: 4 µl buffer 5×(250 mM Tris-HCl pH 8.3; 350 mM KCl; 15 mM MgCl$_2$; 0.1 M DTT); 1 µl of Oligo (dT) 500 µg/ml; 2 µl DTT 0.1 M.; 1 µl 10 mM dNTPs; 5 µg total ARN and completing with 20 µl H$_2$O.

Example 3

Amplification of the specific CDNA encoding the complete hTPO. Amplification of the sequence of interest by "nested PCR" techniques (Polymerase chain reaction). This is done by designing a double pair of primers and a combination of thermostable DNA polymerases in order to amplify the sequence encoding the mature protein that has high specificity and fidelity. In that sense, a high fidelity amplification system was used. This system was composed by the adequate mixture of Taq polymerase and Pow DNA polymerase (EHF; Expand™ High Fidelity PCR System, Boehringer Mannheim). The sequence of primers used in the two amplification rounds are described in Table II. The amplification reactions were performed in a total volume of 100 µl by adding:

2 µl (dNTPs 200 □M)
3 µl (10 mM forward primer)
3 µl (10 mM reverse primer)
10 µl (buffer 10×)
0.75 µl (Thermostable polymerases EHF)
5 µl (cDNA)
76.25 µl (H$_2$O)

The first round of amplification was performed with the external primers TPO$_{EXT-FOW}$ y TPO$_{EXT-REV}$ (see Table II A) and the reaction was then incubated for 30-amplification cycle (previously incubated for 2 minutes at 95° C.).

Cycles 1-10: 30 sec. at 95° C. 30 sec. at 58° C. and 120 sec. at 72° C.
Cycles 10-20: 30 sec. at 95° C. 30 sec. at 58° C. and 240 sec. at 72° C.
Cycles 20-30: 30 sec. at 95° C. 30 sec. at 58° C. and 360 sec. at 72° C.
Final elongation stage: 10 minutes at 72° C.

The second round of amplification was performed with the internal primers TPO$_{FOW}$ y TPO$_{REV}$ (see Table II B) under the same conditions, but substituting 5 µl of cDNA of the first round for 2 µl of the first amplification reaction. The reaction conditions were 20 cycle of amplification with previous incubation for 2 minutes at 95° C., described as follows:

Cycles 1-10: 30 sec. at 95° C. 30 sec. at 62° C. and 120 sec. at 72° C.
Cycles 10-15: 30 sec. at 95° C. 30 sec. at 62° C. and 240 sec. at 72° C.
Cycles 15-20: 30 sec. at 95° C. 30 sec. at 62° C. and 360 sec. at 72° C.
Final elongation stage: 10 minutes at 72° C.

Example 4

Purification and preparation of amplified cDNA of hTPO in order to be cloned. The amplified product is separated and identified by electrophoresis, in an agarose gel of low fusion point (1%). The part of the gel containing the band of 1107 base pairs was cut and the DNA was isolated and purified (Nucleiclean, Sigma). This was carried out performing techniques that use the capacity of fiber-glass microspheres in order to strongly bind the DNA in a saturated sodium iodide media which at the same time is capable of dissolving the agarose (16). The DNA is extracted with phenol/chloroform, ethanol washed, precipitated with ethanol, being finally resuspended in 10 ul of H$_2$O. In order to incorporate adenine nucleotides at the 3'OH extremes, for cloning in A-T vectors, the purified fragment is incubated for 10 minutes at 72° C. with: Taq DNA polymerase, buffer and dATP. The fragment is again extracted and purified using phenol/chroloform extraction, precipitated in ethanol and then resuspended in 20 µl of H$_2$O. The cDNA fragment is ready to be ligated and cloned into an A-T cloning vector system.

Example 5

Cloning of amplified cDNA fragment into an A-T cloning vector system. The purified fragment of experiment 4 was ligated to pCR 2.1 plasmid (Original TA Cloning Kit; Invitrogen). The ligation was performed using T4 DNA ligase (Boehringer Mannheim), pCR2 vector and the purified cDNA hTPO, in a saline medium according to the following:

2 µl of TPO fragment purified in Example 4.
1 µl of ligation buffer 10×
2 µl of pCR2.1 vector (25 ng/µl)
1 µl of T4 DNA ligase (4 units)
4 µl of H$_2$O The enzymatic ligation was incubated for 16 hours at 14° C.

Competent *E. Coli* strains (ONE SHOT™ TOP10F'; Invitrogen) were transformed with the ligated plasmid. This vectors allowed: a) obtaining bacterial colonies that included the plasmid, due to the presence of the resistance gene to ampicillin; b) identifying bacterial colonies with plasmids containing cDNA inserts encoding hTPO. This is performed depending on the presence of the lacZα□gene in the vector, which is inducible by IPTG isopropylthio-β-galactoside), allowing to trace them, identifying the bacterial colonies white/blue according to X-Gal hydrolysis; c) isolation of high quantities of plasmids (minipreps) from positive bacterial colonies by minicultures in LB (Luria-Bertani) in order to perform restriction analysis and sequenciation of the inserts using M13 primers in order to verify the sequence. After restriction analysis 10 positive colonies are obtained, correlatively called pCR2 TPO-1 to pCR2 TPO-10.

The isolated colonies were segregated into three groups:
Clones pCR2-1, -2, -4 and -9 matching the corresponding sequence of hTPO, where 12 bases were deleted (4aa), identical to the previously described isoform called TPO2 (17).

Clones pCR2-5, -6, -7, -8 and -10 matching a complete sequence of native hTPO, with no aminoacidic substitution.

Clone pCR2-9 matches the corresponding sequence of hTPO, with a deletion of 116 bp identical to the previously described isoform TPO3 (17).

The inserts were sequenced, in order to be correctly identified, according to the method described by Sanger and cols. (18) The sequenciation was performed completely over both DNA strands.

The plasmid preparation corresponding to clone pCR2 TPO-5 was selected to continue the following experimental steps.

Example 6

Vector design with the sequence encoding mature hTPO (pK-eTPO). An eukaryotic expression vector was constructed, according to the following characteristics:
1. Neomycin-resistance gene (Neo$^r$) to positively select the transfected cells in a medium that contains neomycin (G-418)
2. Promoter sequence for immunoglobulins genes
3. A cloned region containing the restriction sites Cla I and Not I
4. Enhancer of human immunoglobulin transcription
5. Prokaryotic replication origin for *E. Coli* (ColE1 ori)
6. Ampicillin-resistance gene (Amp$^r$)
7. Eukaryotic replication origin derived from SV 40 (SV 40 ori)

All these sectors are logically ordered to assure transcription and transduction of the corresponding rhTPO gene. The construction of the expression vector was identified as pK and can be graphically observed in FIG. 1.

Example 7

Construction of an eukaryotic expression vector using the sequence encoding mature hTPO (pK-eTPO) The construction of the pK expression vector that has the DNA fragment encoding hTPO and whose sequence was totally verified was called pK-eTPO. A graphic map of pK-eTPO structure, including all functional segments is depicted in FIG. 1. The construction was performed in the following experimental stages:

Stage 1

First, expression primers containing the Cla I and Not I restriction sites were designed (see Table II C), and were called Cla-eTPO$_{FOW}$ and Not-eTPO$_{REV}$. They allow to:
1) Amplify the sequence that codes hTPO that is contained in the cloning vector obtained from pCR2 TPO-5.
2) Introduce two restriction sited (Cla I and Not I in order to introduce the complete sequence encoding hTPO including its signal peptide in pK vector after an enzymatic ligation reaction.

The amplified hTPO fragment that is contained in pCR2 TPO-5, and that was modified to contain the Cla I and Not I restriction sites, was called eTPO-5. The amplification reaction was performed in a total volume of 50 µl (Taq DNA polymerase kit; Gibco BRL-Life Technologies):
  2.5 RI (dNTPs 10 mM)
  2.5 µl (10 mM of Cla-eTPO$_{FOW}$)
  2.5 µl (10 mM of Not-eTPO$_{REV}$)
  5 µl (buffer 10×)
  0.5 µl (Taq polymerase)
  5 µl (dilution 1/100.000 of pCR2 TPO-5)
  1.5 µl MgCl$_2$ (50 mM)
  30.5 µl (H$_2$O)

Incubation conditions: one 4-minute cycle at 95° C.; 25 cycles at 95° C. 30", 65° C. 30", 72° C. 30"; and one final elongation cycle of 10 min. at 72° C.

Stage 2

The amplified product is separated and identified using electrophoresis techniques in an agarose gel low fusion (1%). The part of the gel containing the band of 1090 bp was cut and the DNA was isolated and purified (Nucleiclean, Sigma). This was carried out by performing techniques that use the capacity of fiber-glass microspheres in order to strongly bind the DNA in a saturated sodium iodide media which at the same time is capable of dissolving the agarose (16). Then the DNA is extracted with phenol/chloroform and washed, precipitated with ethanol, being finally resuspended in 15 µl of H$_2$O.

Stage 3

The purified eTPO fragment is ligated into the pCR2-1 vector in order to perform enzymatic restriction analysis and nucleotide sequenciation to verify the complete identity of the fragment with the native hTPO according to the following reaction scheme:
  1 µl eTPO fragment.
  1 µl ligation buffer 10×
  2 µl pCR2.1 vector (25 ng/µl)
  1 µl T4 DNA ligase (4 units)
  5 µl H$_2$O The reaction is incubated for 16 hours at 4° C. The ligation product is used to transform competent *E. Coli* strains (ONE SHOT™ TOP10F'; Invitrogen) to allow their expansion according to the vendor's technical specifications. Six bacterial colonies containing the correct plasmid bearing eTPO inserts were identified and isolated. They were called pCR2-eTPO 1 to 6. Minicultures in LB medium with ampicillin were performed in each of them, in order to isolate the plasmidic material (minipreps).

Stage 4

Inserts eTPO-1 to 6 were identified and sequenced. This was done using the BamH I restriction profile and then sequenced to verify the complete nucleotide sequence in both DNA strands using the method described by Sanger and cols. (18) in an automated sequenciator (ALF-EXPRESS; Pharmacia). Table I shows the nucleotide sequence identified as "ETPO", that corresponds to pCR2-eTP02 plasmid, compared to sequence NM000460 (Sauvage et al., 1994). As depicted, the obtained sequence is identical to the one used as reference. The pCR2-eTPO2 plasmid was selected to carry out the subsequent stages.

Stage 5

The eukaryotic pK expression vector was enzymatically digested using Cla I and Not I before it was ligated to the eTPO fragment. To perform the digestion, the enzymatic reaction was incubated for 4 hours at 37° C. as follows:
  10.0 µl of vector pK plasmid preparation
  2.0 µl of Cla I enzymatic preparation (Sigma)
  1.5 µl of Not I enzymatic preparation (Sigma)
  5.0 µl of buffer 10×
  31.5 µl of H$_2$O The linearized vector, after enzymatic digestion, is separated and identified using electrophoresis techniques with low fusion agarose gel (1%). The region, in which the vector was contained, was cut and DNA was isolated and purified by electroelution in dialysis membranes. The DNA is extracted with phenol/chloroform, washed, and ethanol precipitated, being finally resuspended in 15 μl H₂O.

Stage 6

The pCR2-eTPO2 was enzymatically digested using Cla I and Not I in order to obtain the eTPO-2 fragment. For the digestion the following enzymatic reaction was used which was incubated for 4 hours at 37° C.:

5.0 μl of plasmidic preparation of pCR2-eTPO 2
2.0 μl of enzymatic preparation of Cla I (Sigma)
1.5 μl of enzymatic preparation of Not I (Sigma)
5.0 μl of buffer 10×
36.5 μl of H₂O The linearized vector, after enzymatic digestion, is separated from the eTPO 2 fragment using electrophoresis techniques with low fusion agarose gel (1%). The gel region in which the fragment eTPO 2 is contained was cut and DNA was isolated and purified by techniques that use the capacity of fiber-glass microspheres in order to strongly bind the DNA in a saturated sodium iodide media which at the same time is capable of dissolving the agarose (16). The DNA is extracted with phenol/chloroform, washed, precipitated with ethanol, being finally resuspended in 15 μl of H₂O.

Stage 7

The ligation of pK vector with eTPO-2 purified fragment is performed using T4 DNA ligase (Pharmacia) following the supplier's technical specifications. The product of this ligation, called pK-eTPO, is purified using phenol/chloroform extraction methods, precipitated with ethanol, being finally resuspended in 15 μl H₂O.

Stage 8

Transfection of E. Coli (strain XL1), with the constructed pK-eTPO is performed by electroporation. In a 1 mm cuvette, 40 ul of electro-competents XL-1 strain are placed together with 2 μl of the purified ligation obtained in stage 7. A 1380 v pulse with 129 Ω of resistance, capacitance of 50 μF, was triggered for 5 milliseconds. After the pulse, 800 μl of LB medium are added. After an incubation period of 45 min. at 37° C., in an orbital incubator at 200 rpm, LB-agar-ampicillin dishes are seeded.

Two positive colonies are isolated, and expanded in LB-ampicillin overnight minicultures. Plasmids were extracted using conventional methods ("minipreps") in order to verify the inserts, by amplification and restriction enzyme analysis. In this way a purified plasmid fraction of pK-eTPO was obtained.

Example 8 pKeTPO vector linearization with Puv I and selection of the mammalian cell line to be transfected. Once pK-eTPO is obtained, the mammalian cell line derived from murine myeloma known as X-63 (P3X63Ag8.653, ATCC N° CRL 1580), was selected, although any cell that is derived from a mammal can be eventually used with this expression plasmid. Among the different cell lines, this one was selected as it has the following advantages: a) it has a high-efficacy synthesis and secretory system of proteins (immunoglobulins) that perfectly adapt to the designed expression vector, in the present invention, as it includes a promoter of immunoglobulins genes associated to an immunoglobulin transcription enhancer. Additionally is capable of undefinitively grow in in vitro culture media such as RPMI-1640 supplemented with fetal bovine serum (FBS) 10%. pKeTPO vector was linearized with Pvu I (Boehringer Mannheim), according to the following reaction:

20 μl of plasmid pKeTPO fraction
5 μl of buffer H (10×)
2 μl of Pvu I
23 μl of H₂O The reaction was incubated at 37° C. during 4 hours and the material was purified using phenol/chloroform extraction, precipitated with ethanol and finally recovered in 10 μl of H₂O.

Example 9

Transfection of X-63 cells with pKeTPO vector. The mammalian cells (X-63) described in example 8 were expanded in vitro in RPMI-1640 (Gibco BRL-Life Technologies) with 10% FBS, then washed in RPMI-1640 free of FBS. They were resuspended in the following concentrations: 1.5 million of cells in 800 μl RPMI 1640 without FBS. Then, the 800 μl of cells were placed in a 2 mm electroporation cuvette, adding 10 μg of pKeTPO plasmid. The electroporation (BTX Electroporation System 600; Genetronics Biomedical LTD) was performed at 13 msec under the following conditions:

C: 1200 μF; R: 48 Ω; V: 210 V; E: 1.050 kV/cm

The electroporated cells were cultured for 24 hours in RPMI 1640 with 20% FBS at 37° C. and 5% CO₂.

Example 10

Screening and selection of cloned cells producing rhTPO. After transfecting the cells, described in example 9, they were distributed in 3 different culture groups (culture I, II and III) with neomycin (1 mg/ml). The base culture medium was RPMI 1640 with 10% FBS and streptomycin-penicillin (50 mcg/ml and 100 UI/ml respectively), 2 mM L-glutamine 1 uM sodium piruvate and 10 mM Hepes (growth medium). After 15 days of breeding, with a weekly change of culture media, the secretion of rhTPO in supernatants was analyzed performing western-blot using anti-hTPO antibody (RDI; Research Diagnostics, Inc.). As negative controls, supernatants of X-63 transfected cell with pK kappa vector, were used. The proceedures were identical to those of TPO including the kappa human chain of immunoglobulin instead of the rhTPO insert.

Supernatants from culture II resulted weakly positive for rhTPO, and cloning was performed by limit dilution (cell dilution: 0.3 cells/well placed in a 96-well plates in RPMI1640 with 20% of FBS and 1 mg/ml neomycin). After 15 days the 58 neomycin-resistant clones were isolated. Supernatants were processed to evaluate rhTPO presence by western blot. The analysis revealed the presence of 16 clones that produced and secret rhTPO. The clone called 2A4 was isolated, as significant quantities of rhTPO were detected in culture supernatants and was again cloned, by limit dilution, in order to assure its clonaility.

As it is shown in FIG. 2, after analysis by western-blot, subclone 16 from 2A4 was selected, being called subclone 24A-16. The production stability of rhTPO using sub clone 24A-16 was tested after 8 weeks of uninterrupted culture (see FIG. 2). The clone from X-63 cell called 24A-16 and producer of soluble rhTPO in a stable way, will be called Clone X-63 eTPO.

Example 11

Analysis of the presence and biological activity of rhTPO produced in this expression system. Assays testing biological activity were performed in vitro, using the supernatant of X-63eTPO culture at concentrations of 0.6×10⁶ cells/culture in presence of RPMI 1640, 10% FBS:

Determination of TPO concentration by ELISA. An ELISA test was performed using a kit for human TPO (Quantikine, R&D Systems). It was confirmed that approximate concentration, under standard culture conditions, was 0.5 mcg/ml.

In vitro bioassay using the Baf-mpl cell line. The Baf-mpl cell line (deposited Sep. 28, 1994 under the Budapest treaty terms in ATCC N° CRL-11723) corresponds to the murine line Baf-BO3 transfected with the Mpl receptor (TPO receptor). The parental line Baf-BO3 depends on IL-3 and transfected line Baf-mpl depends on IL-3 or TPO. The assay is based on incubating the cells in the presence of different concentrations of cytokines or the supernatant that is being tested during 48 hours. After this period they are incubated with [3$_H$]-Thymidine for twelve hours after which the cells are recovered over a filter and then placed in vials where radioactivity is tested by liquid scintillation counting. Two experiments were performed in 96-well plates testing supernatants at different concentrations: 10%, 3%, 1%, 0.3%, 0.1%, 0.03%, 0.01% and 0.003%, in triplicate over Baf-mpl cells (30.000 cells/well). A dose-dependant curve was performed with standard TPO at 10 ng/ml, 3 ng/ml, 1 ng/ml, 0.3 ng/ml, 0.1 ng/ml, 0.03 ng/ml, 0.01 ng/ml and 0.003 ng/ml concentrations. Internal control test with IL-3 was performed in order to assure that the cell line responds to the analyzed cytokines. A negative control was performed without growth factors. The same was performed with the parental line Baf-BO3 in order to discard an IL-3 effect in the tested supernatants. Experiments showed similar results indicating a rhTPO standard activity of 0.4 mcg/ml in supernatants culture of X-63eTPO.

In vitro proliferation and differentiation of megakaryocytic progenitors from CD34+ bone marrow cells. The bone marrow cells CD34+ were obtained through gradient density centrifugation with Ficoll-Hypaque and then immunomagnetically selected (Miltenyi, Mini-MACS). These cells are cultured in liquid medium under conditions that allow differentiation towards the megakaryocytic lineage. These conditions are: FBS-free Iscove culture media supplemented with transferrine, insulin, bovine seroalbumin, liposomes and in the presence of TPO. CD34+ bone marrow cells were cultured in 24-well plates (100.000 cells/well) with different dilutions of standard rhTPO or supernatant of X-63eTPO clone. After 10 days cell proliferation is tested (number of cells) and percentage of megakaryocytic produced by marking them with FITC-conjugated anti-CD41 monoclonal antibodies and analyzed by flow citometry. Four different concentrations of rhTPO were tested (20 ng/ml, 10 ng/ml, 5 ng/ml, 2.5 ng/ml). It was observed that 70% of the cells were of megakaryocytic lineage (CD41 positive cells). Supernatants from X-63eTPO were tested at 3 different concentrations: 10%, 5% y 2.5%. An increase of 3, 2 and 1.5 times, in cell numbers were respectively observed. Regarding megakaryocytic growth we obtained 75% of CD41 + cells, in the three cases, so the absolute number of megakaryocytes varies according to supernatant's concentration being related to cell proliferation. Representative results analyzed by flow citometry are shown in FIG. 3, where it can be appreciated that 2.5% supernatant culture is capable of inducing an expression level equivalent to that induced by 5 ng/ml of standard hTPO.

TABLE I

Reference nucleotidic and aminoacidic sequence of the hTPO NM 000460 [de Sauvage et al, Nature 369; 533-538 (1994)].

```
SEQ N°1              M  E  L  T  E  L  L  L  V  V  M  L  L  L  T  A
NM 000460 CATATCGATTTCTCACAATGGAGCTGACTGAATTGCTCCTCGTGGTCATGCTTCTCCTAACTGCA
ETPO      ..................................................................
          - - - - - - - - - - - - - - - - - - - - - - - -

SEQ N°1   R  L  T  L  S  S  P  A  P  P  A  C  D  L  R  V  L  S  K  L  L  R
NM 000460 AGGCTAACGCTGTCCAGCCCGGCTCCTCCTGCTTGTGACCTCCGAGTCCTCAGTAAACTGCTTCGT
ETPO      ..................................................................
          - - - - - - - - - - - - - - - - - - - - - - - -

SEQ N°1   D  S  H  V  L  H  S  R  L  S  Q  C  P  E  V  H  P  L  P  T  P  V
NM 000460 GACTCCCATGTCCTTCACAGCAGACTGAGCCAGTGCCCAGAGGTTCACCCTTTGCCTACACCTGTC
ETPO      ..................................................................
          - - - - - - - - - - - - - - - - - - - - - - - -

SEQ N°1   L  L  P  A  V  D  F  S  L  G  E  W  K  T  Q  M  E  E  T  K  A  Q
NM 000460 CTGCTGCCTGCTGTGGACTTTAGCTTGGGAGAATGGAAAACCCAGATGGAGGAGACCAAGGCACAG
ETPO      ..................................................................
          - - - - - - - - - - - - - - - - - - - - - - - -

SEQ N°1   D  I  L  G  A  V  T  L  L  L  E  G  V  M  A  A  R  G  Q  L  G  P
NM 000460 GACATTCTGGGAGCAGTGACCCTTCTGCTGGAGGGAGTGATGGCAGCACGGGGACAACTGGGACCC
ETPO      ..................................................................
          - - - - - - - - - - - - - - - - - - - - - - - -

SEQ N°1   T  C  L  S  S  L  L  G  Q  L  S  G  Q  V  R  L  L  L  G  A  L  Q
NM 000460 ACTTGCCTCTCATCCCTCCTGGGGCAGCTTTCTGGACAGGTCCGTCTCCTCCTTGGGGCCCTGCAG
ETPO      ..................................................................
          - - - - - - - - - - - - - - - - - - - - - - - -

SEQ N°1   S  L  L  G  T  Q  L  P  P  Q  G  R  T  T  A  H  K  D  P  N  A  I
NM 000460 AGCCTCCTTGGAACCCAGCTTCCTCCACAGGGCAGGACCACAGCTCACAAGGATCCCAATGCCATC
ETPO      ..................................................................
          - - - - - - - - - - - - - - - - - - - - - - - -
```

TABLE I-continued

Reference nucleotidic and aminoacidic sequence
of the hTPO NM 000460 [de Sauvage et al, Nature 369; 533-538 (1994)].

```
SEQ N°1    F   L   S   F   Q   H   L   L   R   G   K   V   R   F   L   M   L   V   G   G   S   T
NM 000460  TTCCTGAGCTTCCAACACCTGCTCCGAGGAAAGGTGCGTTTCCTGATGCTTGTAGGAGGGTCCACC
  ETPO     ..................................................................
           -   -   -   -   -   -   -   -   -   -   -   -   -   -   -   -   -   -   -   -   -   -

SEQ N°1    L   C   V   R   R   A   P   P   T   T   A   V   P   S   R   T   S   L   V   L   T   L
NM 000460  CTCTGCGTCAGGCGGGCCCCACCCACCACAGCTGTCCCCAGCAGAACCTCTCTAGTCCTCACACTG
  ETPO     ..................................................................
           -   -   -   -   -   -   -   -   -   -   -   -   -   -   -   -   -   -   -   -   -   -

SEQ N°1    N   E   L   P   N   R   T   S   G   L   L   E   T   N   F   T   A   S   A   R   T   T
NM 000460  AACGAGCTCCCAAACAGGACTTCTGGATTGTTGGAGACAAACTTCACTGCCTCAGCCAGAACTACT
  ETPO     ..................................................................
           -   -   -   -   -   -   -   -   -   -   -   -   -   -   -   -   -   -   -   -   -   -

SEQ N°1    G   S   G   L   L   K   W   Q   Q   G   F   R   A   K   I   P   G   L   L   N   Q   T
NM 000460  GGCTCTGGGCTTCTGAAGTGGCAGCAGGGATTCAGAGCCAAGATTCCTGGTCTGCTGAACCAAACC
  ETPO     ..................................................................
           -   -   -   -   -   -   -   -   -   -   -   -   -   -   -   -   -   -   -   -   -   -

SEQ N°1    S   R   S   L   D   Q   I   P   G   Y   L   N   R   I   H   E   L   L   N   G   T   R
NM 000460  TCCAGGTCCCTGGACCAAATCCCCGGATACCTGAACAGGATACACGAACTCTTGAATGGAACTCGT
  ETPO     ..................................................................
           -   -   -   -   -   -   -   -   -   -   -   -   -   -   -   -   -   -   -   -   -   -

SEQ N°1    G   L   F   P   G   P   S   R   R   T   L   G   A   P   D   I   S   S   G   T   S   D
NM 000460  GGACTCTTTCCTGGACCCTCACGCAGGACCCTAGGAGCCCCGGACATTTCCTCAGGAACATCAGAC
  ETPO     ..................................................................
           -   -   -   -   -   -   -   -   -   -   -   -   -   -   -   -   -   -   -   -   -   -

SEQ N°1    T   G   S   L   P   P   N   L   Q   P   G   Y   S   P   S   P   T   H   P   P   T   G
NM 000460  ACAGGCTCCCTGCCACCCAACCTCCAGCCTGGATATTCTCCTTCCCCAACCCATCCTCCTACTGGA
  ETPO     ..................................................................
           -   -   -   -   -   -   -   -   -   -   -   -   -   -   -   -   -   -   -   -   -   -

SEQ N°1    Q   Y   T   L   F   P   L   P   P   T   L   P   T   P   V   V   Q   L   H   P   L   L
NM 000460  CAGTATACGCTCTTCCCTCTTCCACCCACCTTGCCCACCCCTGTGGTCCAGCTCCACCCCCTGCTT
  ETPO     ..................................................................
           -   -   -   -   -   -   -   -   -   -   -   -   -   -   -   -   -   -   -   -   -   -

SEQ N°1    P   D   P   S   A   P   T   P   T   P   T   S   P   L   L   N   T   S   Y   T   H   S
NM 000460  CCTGACCCTTCTGCTCCAACGCCCACCCCTACCAGCCCTCTTCTAAACACATCCTACACCCACTCC
  ETPO     ..................................................................
           -   -   -   -   -   -   -   -   -   -   -   -   -   -   -   -   -   -   -   -   -   -

SEQ N°1    Q   N   L   S   Q   E   G   #
NM 000460  CAGAATCTGTCTCAGGAAGGGTAAGCGGCCGCTCT
  ETPO     ...................................
           -   -   -   -   -   -   -   -
```

(.) identical nucleotidic sequence
(-) identidad aminoacidic sequence
(#) stop codon
ETPO represent de sequence of hTPO obtained in the present invention
Secretory peptide is depicted in bold characters.
Internal primers are represented in underlined characters

TABLE II

Sequence of primers used to amplify human TPO

A. Primers used in the first round of the nested PCR.

TPO$_{EXT-FOW}$.                    GAG GAA GGA TTC AGG GGA GAG G
                                                 (SEQ ID NO:3)
(External forward primer)

TPO$_{EXT-REV}$.                    GGA AGG GAG CTG TAC ATG AGA C
                                                 (SEQ ID NO:4)
(External reverse primer)

TABLE II-continued

Sequence of primers used to amplify human TPO

B. Primers used in the second round of the nested PCR.

TPO_FOW.                       AGC CAC GCC AGC CAG ACA CCC C
                               (SEQ ID NO:5)
(Internal forward primer)

TPO_REV.                       GCA GTG TCT GAG AAC CTT ACC C
                               (SEQ ID NO:6)
(Internal reverse primer)

C. Primers used to insert the restriction sites
ClaI y Not I into the DNA fragment encoding hTPO.

Cla-eTPO_FOW.                  CAT ATC GAT TTC TCA CAA TGG AGC TGA CTG AAT TGC TCC
                               (SEQ ID NO:7)
Not-eTPO_REV.                  AGA GCG GCC GCT TAC CCT TCC TGA GAC AGA TTC TGG G
                               (SEQ ID NO:8)

BIBLIOGRAPHIC REFERENCES

1. Kuter, D. J. 1996. Thrombopoietin: Biology and Clinical Applications. *The Oncologist* 1:98.
2. Kelemen, E., I. Cserhati, and B. Tanos. 1958. Demonstration and some properties of human thrombopoietin in thrombocythemic sera. *Acta Haematol.* (Basel) 20:350.
3. Souyri, M., I. Vigon, J. F. Penciolelli, J. M. Heard, P. Tambourin, and F. Wendling. 1990. A putative truncated cytokine receptor gene transduced by the myeloproliferative leukemia virus immortalizes hematopietic progenitors. *Cell* 63:1137.
4. Bartley, T. D., J. Bogenberger, P. Hunt, Y. L. Li, H. S. Lu, F. Martin, M. S. Chang, B. Samai, J. L. Nichol, S. Swift, M. J. Johnson, R. Y. Hsu, V. P. Parker, S. Suggs, J. D. Skrine, L. A. Merewether, C. Clogston, E. Hau, M. M. Hokom, A. Hornkohl, E. Choi, M. Pangelinan, Y. Sun, V. Mar, J. McNinch, L. Simonet, F. Jacobsen, C. Xie, J. Shutter, H. Chute, R. Basu, L. Selander, D. Trollinger, L. Sieu, D. Padilla, G. Trail, G. Elliott, R. Izumi, T. Covey, J. Crouse, A. Garcia, W. Xu, J. Del Castillo, J. Biron, S. Cole, H. MC. T., R. Pacifici, I. Ponting, C. Saris, D. Wen, Y. P. Yung, H. Lin, and R. A. Bosselman. 1994. Identification and cloning of a megakaryiocyte growth and development factor that is a ligand for the cytokine receptor Mpl. *Cell* 77:1117.
5. de Sauvage, F. J., P. E. Hass, S. D. Spencer, B. E. Malloy, A. L. Gurney, S. A. Spencer, W. C. Darbonne, W. J. Henxel, S. C. Womg, W. J. Kuang, K. J. Oles, B. Hultgren, L. A. Solberg Jr, D. V. Goeddel, and D. L. Eaton. 1994. Stimulation of megacaryocytopoiesis and thrombopoiesis by the c-mpl ligand. *Nature* 369:533.
6. Kaushansky, K., S. Lok, R. D. Holly, V. C. Broudy, N. Lin, M. C. Bailey, J. W. Forstrom, M. M. Buddle, P. J. Oort, F. S. Hagen, G. J. Roth, T. Papayannopoulou, and D. C. Foster. 1994. Promotion of megakaryocyte progenitor expansion and differentiation by the c-Mpl ligand thrombopoietin. *Nature* 369:568.
7. Lok, S., K. Kaushansky, R. D. Holly, J. L. Kuijper, C. E. Lofton-Day, P. J. Oort, F. J. Grant, M. D. Heipel, S. K. Burkhead, J. M. Kramer, L. A. Bell, C. A. Sprecher, H. Blumberg, R. Johnson, D. Prunkard, A. F. Ching, S. L. Mathewes, M. C. Bailey, J. W. Forstrom, M. M. Buddle, S. G. Osborn, S. J. Evans, P. O. Sheppard, S. R. Presnell, P. J. O'Hara, F. S. Hagen, G. J. Roth, and D. C. Foster. 1994. Cloning and expression of murine thrombopoietin CDNA and stimulation of platelet production in vivo. *Nature* 369:565.
8. Wendling, F., E. Maraskovsky, N. Debill, C. Florindo, M. T pe, M. Titeux, N. Methia, J. Breton-Gorius, D. Cosman, and W. Vainchenker. 1994. c-Mpl ligand is a humoral regulator of megakaryocytopiesis. *Nature* 369:571.
9. Kaushansky, K. 1995. Thrombopoietin: The primary regulator of platelet production. *Blood* 86:419.
10. Leonard, J. P., C. M. Quinto, M. K. Kozitza, T. Y. Neben, and S. J. Goldman. 1994. Recombinant human interleukin-11 stimulates multilineage hematopoietic recovery in mice after a myelosuppressive regimen of sublethal irradiation and carboplatin. *Blood* 83:1499.
11. Foster, D. C., C. A. Sprecher, and F. J. Grant. 1994. Human thrombopoietin: gene structure, cDNA sequence, expression, and chromosomal localization. *Proc. Natl. Acad. Sci. USA* 91:13023.
12. Gurney, A. L., W. J. Kuang, M. H. Xie, B. E. Malloy, D. L. Eaton, and F. J. de Sauvage. 1995. Genomic structure, chromosomal localization and conserved alternative splice forms of thrombopoietin. *Blood* 85:981.
13. Wigler, M., A. Pellicer, S. Silverstein, and R. Axel. 1978. Biochemical transfer of single-copy eucaryotic genes using total cellular DNA as donor. *Cell* 14:725.
14. Neumann, E., M. Schaefer-Ridder, Y. Wang, and P. H. Hofschneider. 1982. Gene transfer into mouse lyoma cells by electroporation in high electric fields. *EMBO J.* 1:841.
15. Chomczynski, P., and N. Sacchi. 1987. Single-step method of RNA isolation by acid guanidinium thiocyanate-phenol-chloroform extraction. *Anal. Biochem.* 162:156.
16. Vogelstein, B., and D. Gillespie. 1979. Preparative and analytical purification of DNA from agarose. *Proc. Natl. Acad. Sci. USA* 76:615.
17. Kuter, D. J., P. Hunt, W. Sheridan, and D. Zucker-Franklin. 1997. Thrombopoiesis and Thrombopoietin: *Molecular, Cellular, Preclinical, and Clinical Biology*. Humana Press Inc.
18. Sanger, F., S. Nicklen, and A. R. Coulson. 1977. DNA sequencing with chain-termninating inhibitors. *Proc. Natl. Acad. Sci.* (*USA*) 74:5463.

We claim:

1. An expression vector replicable in mammalian cells, comprising the following elements grouped in a way that assures a correct and efficient transcription of a fragment comprising the complete sequence encoding the human thrombopoictin (hTPO) polypeptide including its signal peptide (eTPO):
   (i) a hTPO transcription portion consisting of:
      a) a transcription promoter of a variable kappa gene of human immunoglobulins
      b) a DNA segment encoding the complete hTPO polypeptide including its signal peptide
      c) an initnunoglobulin transcription enhancer DNA segment of the human kappa gene in a 3' location with respect to hTPO gene, wherein said enhancer DNA segment consists of the DNA sequence 5' to the Ck region of the human kappa gene
      d) a transcription terminator
      e) a polyadenylation signal; and
   (ii) gene encoding resistance to the antibiotic neomicyn type drugs
   (iii) a gene encoding resistance to the antibiotic ampicillin; and
   (iv) a replication origin for E Coli (ColEI ori).

2. A cultured cell line derived from the munine myeloma called X-63 (ATCC: P63X63Ag8.6533, CRL 1580), which has been stably transfected by the expression vector described in claim 1, and tat is capable of producing and secreting the mature recombinant human thrombopoietin (rhTPO) polypeptide towards the culture media in a biologically active form.

3. A method for obtaining a recombinant polypeptide corresponding to human thrombopoietin (hTPO), comprising the steps of:
   (a) stably transfecting a cultured cell line derived from the murine myeloma called X-63 (ATCC; P63X63Ag8.6533, CRL 1580) with the expression vector described in claim 1, and
   (b) expressing the mature recombinant human thrombopoietin polypeptide.

* * * * *

UNITED STATES PATENT AND TRADEMARK OFFICE
CERTIFICATE OF CORRECTION

PATENT NO. : 7,371,569 B2  Page 1 of 1
APPLICATION NO. : 10/362882
DATED : May 13, 2008
INVENTOR(S) : Alfonso Cayota Guzicovsky et al.

It is certified that error appears in the above-identified patent and that said Letters Patent is hereby corrected as shown below:

IN THE CLAIMS:

Column 25, line 32, delete "thrombopoictin" and replace with "thrombopoietin".
Column 25, line 39, delete "initnunoglobulin" and replace with "immunoglobulin".
Column 26, line 30, delete "munine" and replace with "murine".
Column 26, line 33, delete "tat" and replace with "that".

Signed and Sealed this

Sixth Day of January, 2009

JON W. DUDAS
*Director of the United States Patent and Trademark Office*